United States Patent [19]

Yasuda et al.

[11] 4,339,201
[45] Jul. 13, 1982

[54] TEMPERATURE CONTROL SYSTEM FOR AN ELEMENT ANALYZER

[75] Inventors: Makoto Yasuda; Seiichi Murayama, both of Kokubunji; Masaru Ito, Kodaira, all of Japan

[73] Assignee: Hitachi, Ltd., Tokyo, Japan

[21] Appl. No.: 136,285

[22] Filed: Apr. 1, 1980

[30] Foreign Application Priority Data

Apr. 2, 1979 [JP] Japan .................................. 54-38378

[51] Int. Cl.³ .............................................. G01J 3/30
[52] U.S. Cl. .................................................. 356/312
[58] Field of Search .............................. 356/364–365, 356/307, 311–318; 250/225

[56] References Cited

U.S. PATENT DOCUMENTS 4,035,083  7/1977  Woodriff et al. .................... 356/307
4,128,336 12/1978  Butler .................................. 356/307
4,165,937  8/1979  Murayama et al. ................. 356/312

OTHER PUBLICATIONS

Watne et al., "A Very Inexpensive Temperature Monitor for Flameless Atomic Absorption Apparatus", Applied Spectros copy, vol. 30, #1, 1976, pp. 71–72.
Hudson, K. C., "Temperature Control Circuit", RCA Tech. Notes, TN#806, Mailed 12-11-68.

Primary Examiner—William H. Punter
Attorney, Agent, or Firm—Craig and Antonelli

[57] ABSTRACT

Disclosed is a system for controlling the temperature of an atomizer for an element analyzer, said system comprising a birefringent prism arranged on the optical axis of radiant light emitted out of the atomizer, and a light sensor for detecting the radiant light which passes through said birefringent prism.

8 Claims, 4 Drawing Figures

4,339,201

TEMPERATURE CONTROL SYSTEM FOR AN ELEMENT ANALYZER

BACKGROUND OF THE INVENTION

1. Field of the Invention

This invention relates to a system for controlling the temperature of an atomizer for an element analyzer.

2. Description of the Prior Art

There has been so far known a spectroscopic analyzer which is based on the Voigt effect or Zeeman effect, for example, as disclosed in the Japanese Patent Laid-Open No. 90871/76. Such an analyzer requires an atomizer to change a sample into its atomized vapor state. In the atomizer, in this case, the sample is heated to effect its conversion to the atomized vapor condition.

In a known system of controlling the temperature of such an atomizer, the current which flows through the heater (resistor) in the atomizer is adjusted to a predetermined value. In a further known system of this kind, a light sensor such as a photodiode which is provided in the vicinity of the external wall of the atomizer, is used to measure the intensity of radiant light emitted from the external wall of the atomizer in order to control the current through the atomizer. However, the former system has a defect in that, since the contact resistance between the atomizer and the associated electrodes used to supply current thereto changes with the atomizer condition, even keeping constant the current through the electrodes will cause a change in the atomizer temperature due to the heat developed at the contacts between the atomizer and the electrodes, whereby the exchange of the atomizer for a new one does not ensure that the new one will be placed under the temperature state at the time of the former. Further, the former system has another defect in that, since the wall of the atomizer becomes thinner as the atomizer is used, a constant current supplied to the atomizer will provide a temperature higher than a target temperature for the atomizer. On the other hand, in the latter system, it is also difficult to know accurately the temperature of the internal wall, since the external wall of the atomizer is different in temperature from the internal wall thereof. This is because the temperature of the external wall depends greatly upon the flow rate or velocity of the sheath gas. In addition, in the latter system, the external wall of the atomizer has a much longer life than the internal wall thereof, thereby providing a change in the emissivity of the external wall. This leads to such a defect that even if radiant light from the external wall is monitored accurately, it is difficult to control accurately the temperature in the atomizer.

SUMMARY OF THE INVENTION

It is an object of the present invention to provide a temperature control system for an atomizer, in which a light sensor directly detects radiant light emitted out of the atomizer in order to control accurately the temperature in the atomizer according to the output from the light sensor.

To achieve the above object, the present invention is characterized by a beam splitter or birefringent prism which functions to guide the radiant light from the interior of the atomizer to the light sensor.

DESCRIPTION OF THE PREFERRED EMBODIMENTS

Figure 1:
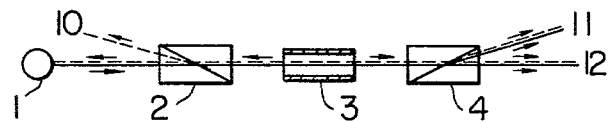
FIG. 1 is the basic arrangement of a temperature control system in accordance with the present invention which is based on the Voigt effect, for explanation of the principle thereof.

Turning now to the drawings, there is shown in FIG. 1 a schematic view for explanation of the principle of the temperature control system for an atomizer according to the present invention, which is based on the Voigt effect. In the figure, birefringent prisms 2 and/or 4 such as Rochon prisms are arranged on the optical axis of a light emitted from a light source 1 at either or both sides of an atomizer 3, and these elements act to direct the incident light in different directions according to the plane of polarization. The light emitted from the light source 1 passes through the prism 2 into the atomizer 3. The light which has passed through the atomizer 3 is directed via the prism 4 (along the solid lines in FIG. 1) to a signal detection system (not shown). On the other hand, a radiant light emitted out of the atomizer 3 is changed to linearly polarized lights at the prisms 2 and 4 and arrives at 1, 10 or 11, 12, along the broken lines in FIG. 1. More specifically, the radiant light emitted from the atomizer 3, at the side of the light source 1, is divided at the birefringent prism 2 into two beams (each is equal in light amount), one is directed to the light source 1 and the other is directed to a position 10. This means that positioning of a light sensor at position 10 allows detection of the amount of radiant light emitted out of the atomizer 3, that is, the output associated directly with the internal temperature of the atomizer. In a similar way, a radiant light emitted out of the atomizer 3, at the side of the atomizer opposite to the light source 1, is divided at the prism 4 into two beams (each is also equal in light amount), each arrives at 11 and 12. Therefore, the radiant light from the atomizer 3 may be detected at 11 and 12.

Figure 2:
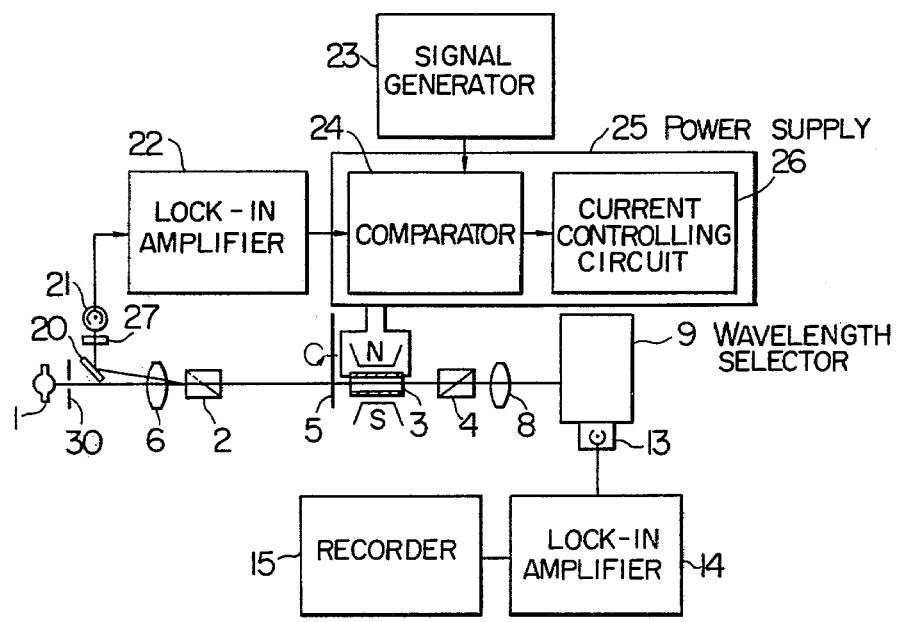
FIG. 2 is the arrangement of the temperature control system in accordance with a first embodiment of the present invention which is based on the Voigt effect and is adaptable for use as an element analyzer.

FIG. 2 is the configuration of the temperature control system according to an embodiment of the present invention, which is based on the Voigt effect and is adaptable for use as an element analyzer. In the illustrated embodiment, the radiant light from the atomizer is detected at the side of the light beam source 1 as shown in FIG. 1. A light from the light source 1 enters the atomizer 3 through a slit 30, a lens 6, a Rochon prism 2 and a chopper 5. The atomizer 3 is placed in the magnetic field which is formed by a pair of magnets N and S. A power supplying circuit 25 is provided to heat the atomizer 3 to put a sample within the atomizer into the atomized vapor state. Presence of such atomized vapor will cause the light with the wavelength inherent to the atom to be elliptically polarized. For this reason, the light passing through the atomizer is elliptically polarized in the atomized vapor atmosphere and enters into the Rochon prism 4. The Rochon prism 4 acts to pass only the polarized component normal to the incident light, which component may then be converted into an electric signal at a light sensor 13 such as a photomultiplier tube or a photodiode, via a lens 8 and a wavelength selector 9 (a spectroscope or an interference filter). This electric signal is sent to a lock-in amplifier 14 which amplifies the signal to record it at a recorder 15. On the other hand, the radiant light out of the atomizer at the side of the light source is interrupted at a chopper 5 and then passes through a Rochon prism 2 and a lens 6 into a mirror 20 which directs the incident light to a light sensor 21, such as a photomultiplier tube or a photodiode. The light sensor 21 converts the incident light into an electric signal. The output of the light sensor 21 is applied to a lock-in amplifier 22 which amplifies it and supplies it to a power supplying circuit 25 in order to control the temperature of the atomizer. The power supplying circuit 25 consists of a comparator 24 and a current controlling circuit 26. The comparator 24 receives a signal input supplied from the lock-in amplifier 22 and a signal input supplied from a signal generator 23 which generates a voltage signal indicative of a preset temperature, and compares the two inputs to apply the comparator output to the current controlling circuit 26. The current controlling circuit 26 controls the current supplied to the atomizer 3 in response to the comparator output. In this way, the atomizer 3 can be kept at a desired temperature by means of the radiant light from the interior of the atomizer.

Referring again to FIG. 2, the chopper 5 functions to interrupt both the light from the light source 1 and the radiant light from the interior of the atomizer and thus pass the light from the light source at the time of passing the radiant light. In the case that a light sensor 21 detects the light reflected on the chopper 5 from the light source 1, appropriate tilting of the chopper 5 allows the reduction or elimination of such reflected light directly from the light source, thereby minimizing the intensity of the reflected light.

In addition, in the case that ambient light and leakage light from the light source 1 are added to the radiant light from the interior of the atomizer, an interference filter 27 may be arranged between the light sensor 21 and the mirror 20 to eliminate or minimize the undesirable added lights, thereby allowing the detection of the above-mentioned radiant light alone.

Figure 3:
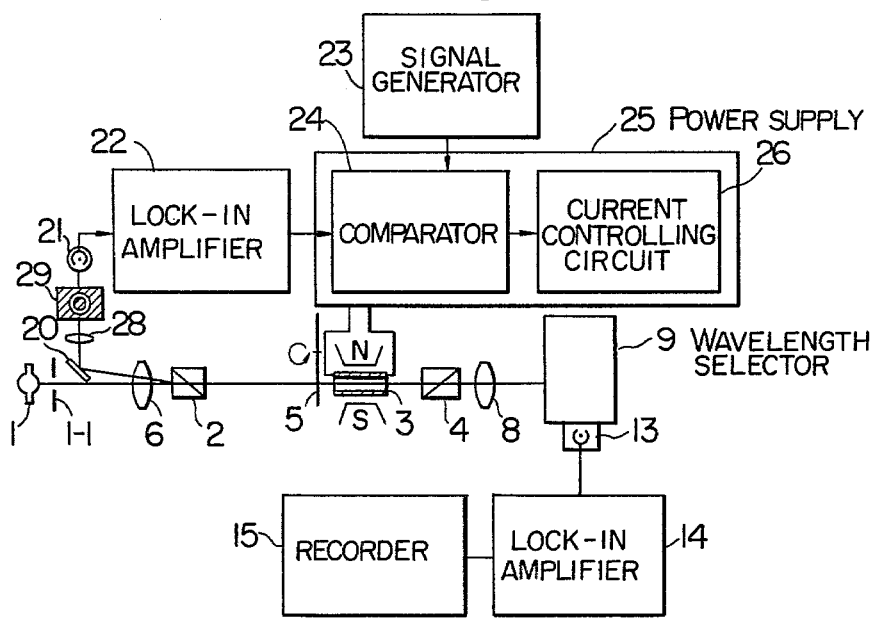
FIG. 3 is the arrangement of the temperature control system in accordance with a second embodiment of the present invention in which the image of the atomizer is focused by means of lenses.

There is shown in FIG. 3 the configuration of the temperature control system according to a second embodiment of the present invention, in which the image of the atomizer is focused by means of lenses. In the illustrated embodiment, parts already described with reference to FIG. 2 are denoted in FIG. 3 by the same reference numerals as in the previous embodiment, except for a lens 28 and ring slit plate 29. The temperature control system of this embodiment is designed suitably for an atomizer the internal wall of which has a circular cross-section. More specifically, in the case that the internal wall of the atomizer 3 has a circular cross-section, the radiant light out of the internal wall of the atomizer 3 is focused on a ring slit plate 29 to form a ring image thereon by means of lenses 6 and 28. In the illustrated figure, the shaded portion on the slit plate 29 indicates the light shielding portion. In this way, since the ring portion on the slit plate 29 is the same as the cross-sectional configuration of the atomizer, only the image through the slit plate 29 can be detected by a light sensor 21. The light received by the light sensor 21, in general, contains the light reflected on the surfaces of a lens 6, a Rochon prism 2 and a chopper 5 and the light scattered from a light source 1. Especially in the case that a light source which produces a great quantity of light such as a xenon (Xe) lamp is employed, the above-mentioned light components become critical. However, provision of the ring slit plate permits the elimination of the above-mentioned light components because they will not be focused on the slit plate. In addition, since the light emitted from the vapor of atoms contained in a sample is focused at the center of the ring slit plate, it can also be removed.

With the arrangement as has been disclosed, the present invention can accomplish an accurately controlled temperature in the atomizer, since the present invention detects the radiant light directly out of the interior of the atomizer to adjust the heating temperature of the atomizer at a desired level.

It will be appreciated that, although the present invention has been described with reference to the embodiments which is based on the Voigt effect (application of this Voigt effect to elemental analysis will be well known by one skilled in the art), the present invention may be applied, in the similar way, to the temperature control system of an atomizer used for an element analyzer which is based on the Faraday effect or for a Zeeman atomic absorption spectrometer.

Further, the present invention may be applied not only to the element analyzer which is based on a magneto-optical effect such as the Voigt effect, or Faraday effect, but also to the usual atomic absorption spectrometer.

Figure 4:
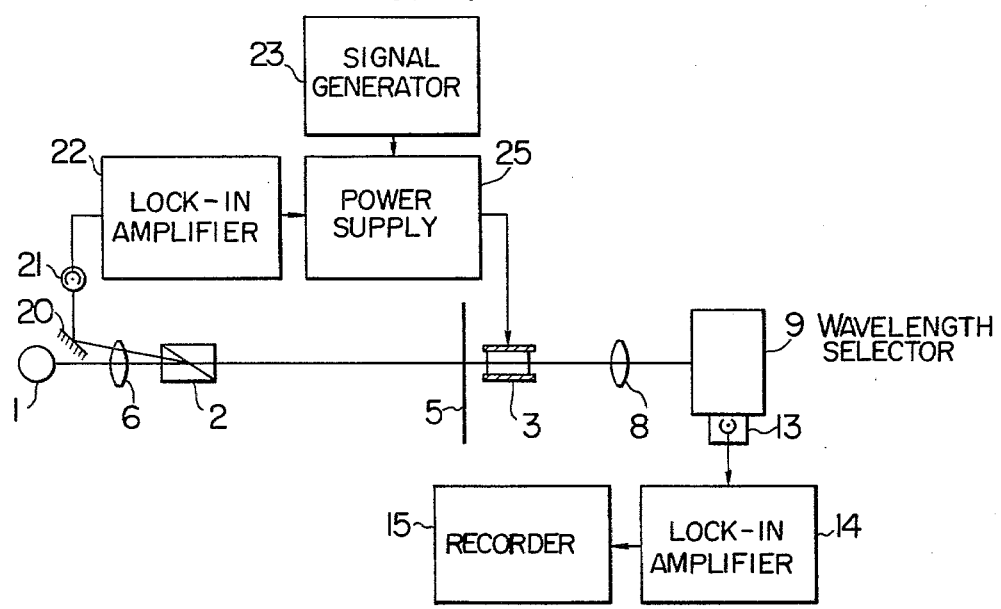
FIG. 4 is the arrangement of the temperature control system in accordance with a third embodiment of the present invention, which is applied to a conventional element analyzer and is the same as that used in a conventional element analyzer except for the temperature control system.

FIG. 4 shows the configuration wherein the present invention is applied to a conventional atomic absorption spectrometer. In the illustrated embodiment, parts already described with reference to FIG. 2 are denoted in FIG. 4 by the same reference numerals as in the previous embodiments and are neglected in the explanation thereof. The configuration in FIG. 4 is the same as that in a conventional element analyzer, except for the temperature control system which consists of a Rochon prism 2, a mirror 20, a light sensor 21, a lock-in amplifier 22, a signal generator 23 and a power supplying circuit 25. For controlling the temperature of the atomizer 3, the above-mentioned explanation holds true. It will be obvious that a well known beam splitter may be employed in place of the Rochon prism in FIG. 4. In FIG. 4, moreover, an interference filter may be used as in the embodiment of FIG. 2 and a slit plate may be used as in the embodiment of FIG. 3.

While the present invention has been described with reference to the preferred embodiments shown in the drawings, it should be understood that the invention is not limited to those embodiments but includes all other possible modifications, alterations and equivalent arrangements within the scope of the appended claims.

We claim:
1. A temperature control system for an element analyzer, comprising:
  a light source for producing light along an optical axis;
  an atomizer positioned along said optical axis for heating a sample placed therein into its vaporized state;
  power supply means connected to said atomizer for supplying power thereto necessary to heat a sample placed therein;

a beam splitter positioned on said optical axis between said light source and said atomizer;

detector means positioned at a point on said optical axis which is on the opposite side of said atomizer from said light source to receive light which has passed through said atomizer and convert said light into an output electrical signal;

light sensor means positioned to receive radiant light which passes from said atomizer through said beam splitter for converting said radiant light into a temperature indicating signal; and control means responsive to said temperature indicating signal for controlling said power supply means to regulate the temperature of said atomizer.

2. A temperature control system for an element analyzer as defined in claim 1 wherein said beam splitter comprises a birefringent prism.

3. A temperature control system for an element analyzer as defined in claim 1 wherein said light sensor means includes a light sensor positioned off said optical axis and means for directing said radiant light passing from said atomizer through said beam splitter to said light sensor.

4. A temperature control system for an element analyzer as defined in claim 3 wherein an interference filter is provided between said beam splitter and said light sensor.

5. A temperature control system for an element analyzer as defined in claim 3 wherein a slit which has the same configuration as the cross-section of said atomizer is provided between said beam splitter and said light sensor.

6. A temperature control system for an element analyzer as defined in claims 1 or 3 wherein said detector means includes wavelength selecting means for selecting at least one wavelength from the light passing through said atomizer and photodetecting means for converting the light at said selected wavelength into said output electric signal.

7. A temperature control system for an element analyzer as defined in claim 6, wherein said detector means includes a further beam splitter positioned on said optical axis on the side of said atomizer opposite said first-mentioned beam splitter.

8. A temperature control system for an element analyzer as defined in claim 1 further including chopper means positioned on said optical axis between said beam splitter and said atomizer for chopping the light passing from said light source to said atomizer via said beam splitter and said radiant light passing from said atomizer to said light sensor means via said beam splitter.

* * * * *